(12) United States Patent
Josse

(10) Patent No.: US 11,744,571 B1
(45) Date of Patent: Sep. 5, 2023

(54) SURGICAL SYSTEM AND METHOD FOR TREATING VERTEBRAL SEGMENTS WITH UNEVEN PEDICLES

(71) Applicant: Warsaw Orthopedic, Inc., Warsaw, IN (US)

(72) Inventor: Loic Josse, Palm Beach Gardens, FL (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/849,899

(22) Filed: Jun. 27, 2022

(51) Int. Cl.
*A61B 17/02* (2006.01)
*A61B 17/70* (2006.01)
*A61B 17/00* (2006.01)
*A61B 17/56* (2006.01)

(52) U.S. Cl.
CPC ........ *A61B 17/025* (2013.01); *A61B 17/0206* (2013.01); *A61B 17/708* (2013.01); *A61B 17/7077* (2013.01); *A61B 2017/00407* (2013.01); *A61B 2017/00477* (2013.01); *A61B 2017/0256* (2013.01); *A61B 2017/564* (2013.01)

(58) Field of Classification Search
CPC ........ A61B 2017/0256; A61B 17/7077; A61B 17/7079; A61B 17/708
See application file for complete search history.

(56) References Cited

U.S. PATENT DOCUMENTS

| | | | |
|---|---|---|---|
| 7,776,051 B2 | 8/2010 | Colleran et al. | |
| 9,211,149 B2 | 12/2015 | Hoefer et al. | |
| 9,402,660 B2 | 8/2016 | Brinkman et al. | |
| 10,363,022 B2 | 7/2019 | Serokosz et al. | |
| 10,898,239 B2 | 1/2021 | Olea et al. | |
| 11,166,707 B2 | 11/2021 | Zakelj et al. | |
| 2006/0247645 A1* | 11/2006 | Wilcox | A61B 17/7077 606/86 R |
| 2014/0012269 A1* | 1/2014 | Bass | A61B 17/025 606/90 |
| 2016/0089188 A1 | 3/2016 | McBride, Jr. et al. | |
| 2017/0311987 A1* | 11/2017 | Bobbitt | A61B 17/7032 |

(Continued)

FOREIGN PATENT DOCUMENTS

| | | | | |
|---|---|---|---|---|
| GB | 2571913 A | * | 9/2019 | ........... A61B 17/708 |
| WO | 2020219015 A1 | | 10/2020 | |

(Continued)

*Primary Examiner* — Eduardo C Robert
*Assistant Examiner* — Tara Rose E Carter
(74) *Attorney, Agent, or Firm* — FOX ROTHSCHILD LLP

(57) ABSTRACT

A surgical system for adjusting a segment of a spine is disclosed. The system may include a rack arm extending in a longitudinal direction from a first end to a second end, and a sliding body portion including a ratcheting mechanism selectively engageable with a spline portion of the rack arm. The system may include a first actuator for translating the sliding body along the rack arm in the longitudinal direction. The system may include a first and second connection tower extending along a first and second axis, respectively, that are each transverse to the longitudinal direction. The system may further include a second actuator including a threaded screw for adjusting the first connection tower along a first axis. In some embodiments, the second actuator is configured to raise and lower the first connection tower in a sagittal plane.

20 Claims, 12 Drawing Sheets

(56) References Cited

U.S. PATENT DOCUMENTS

2020/0054361 A1    2/2020  Peultier et al.
2020/0405359 A1   12/2020  Hayes
2022/0192647 A1*   6/2022  Josse .................. A61B 17/0206

FOREIGN PATENT DOCUMENTS

WO      2020219016  A1    10/2020
WO      2021206723  A1    10/2021

* cited by examiner

SURGICAL SYSTEM AND METHOD FOR TREATING VERTEBRAL SEGMENTS WITH UNEVEN PEDICLES

CROSS-REFERENCE TO RELATED APPLICATIONS

This application incorporates the entire disclosure of U.S. patent application Ser. No. 16/487,057, titled SURGICAL SYSTEM, and filed Aug. 19, 2019.

TECHNICAL FIELD

The present disclosure generally relates to medical devices for the treatment of spinal disorders. Various embodiments may include a surgical system and a method for correction of a spinal disorder related to vertebral segments with uneven pedicles.

BACKGROUND

Spinal disorders, such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation, and implantable prosthetics. Correction treatments used for positioning and alignment of vertebrae may employ spinal implants including spinal constructs and interbody devices for stabilization of a treated section of a spine. In some cases, the spinal implants may be manipulated with surgical instruments for compression and distraction of vertebrae. This disclosure describes an improvement over these prior technologies.

SUMMARY

The techniques of this disclosure generally relate to a system and method for treating the human spine.

In a first aspect, this disclosure relates to a surgical system for adjusting a segment of a spine. The system may include a rack arm extending in a longitudinal direction from a first end to a second end, and a sliding body portion including a ratcheting mechanism selectively engageable with a spline portion of the rack arm, for example. The system may include a first actuator for translating the sliding body along the rack arm in the longitudinal direction, for example. The system may include a first and second connection tower extending along a first and second axis, respectively, that are each transverse to the longitudinal direction, for example. The system may further include a second actuator including a threaded screw for adjusting the first connection tower along a first axis, for example. In some embodiments, the second actuator is configured to raise and lower the first connection tower in a sagittal plane, for example.

In a second aspect, this disclosure relates to a surgical system for adjusting a segment of a spine. The system may include a ratchet having a rack arm extending in a longitudinal direction and a sliding body portion movable along a length of the rack arm in the longitudinal direction, for example. In some embodiments, the sliding body portion may include a pawl engageable with the rack arm, for example. The system may further include an adjustment mechanism having a threaded actuator, for example. The system may further include a first angulation assembly coupled to the adjustment mechanism, and a second angulation assembly coupled to the sliding body portion, for example. The system may further include a first connection tower configured to couple to a first bone fastener, and the first connection tower may extend along a first axis transverse to the longitudinal direction and be pivotally coupled to the first angulation assembly, for example. The system may further include a second connection tower configured to couple to a second bone fastener, and the second connection tower may extend along a second axis transverse to the longitudinal direction and be pivotally coupled to the sliding body portion, for example. In various embodiments, the threaded actuator is configured to translate the first connection tower relative to the rack arm in a sagittal plane, for example.

In a third aspect, this disclosure relates to a method for adjusting a segment of a spine, for example. The method may include the step of receiving a surgical system. The system may include a rack arm extending in a longitudinal direction from a first end to a second end, the rack arm including a spline portion, for example. The system may further include a sliding body portion including a ratcheting mechanism having a first actuator and a pawl selectively engageable with the spline portion of the rack arm, for example. In various embodiments, the first actuator includes a rotatable gear meshed with the spline portion for translating the sliding body along the rack arm in the longitudinal direction, for example. The system may further include, a first connection tower extending along a first axis transverse to the longitudinal direction and being coupled to the rack arm; and a second connection tower extending along a second axis transverse to the longitudinal direction and being coupled to the sliding body portion, for example. The system may further include a second actuator including a threaded screw for adjusting the first connection tower along the first axis, for example. The method may further include the step of implanting a first bone fastener system in a first vertebra; and implanting a second bone fastener system in a second vertebra, for example. The method may further include the step of attaching the first connection tower to the first fastener system; and attaching the second connection tower to the second bone fastener system, for example. The method may further include the step of manipulating the first vertebra by adjusting the second actuator thereby moving the first vertebra in a sagittal plane.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
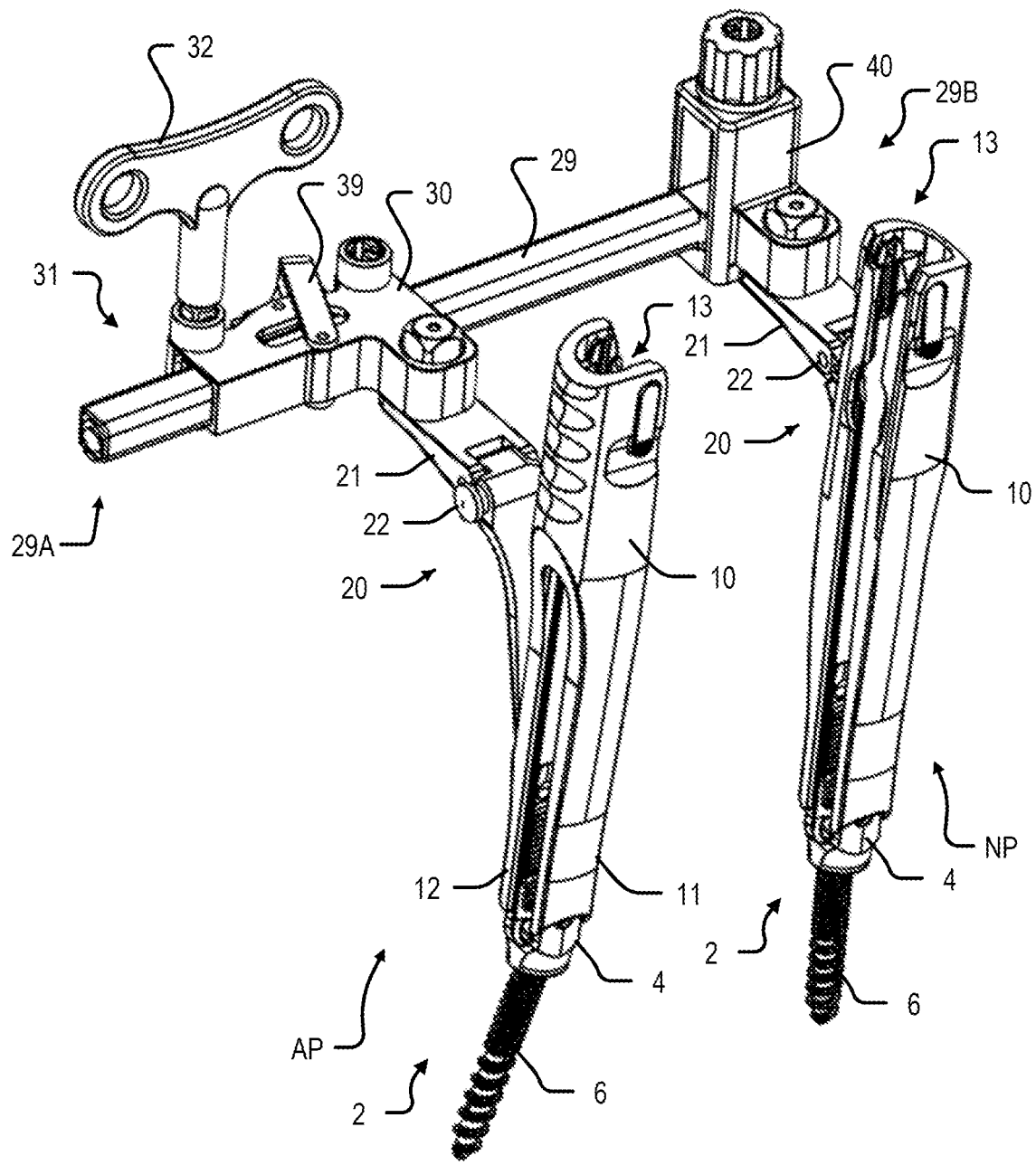
FIG. 1 is a first front perspective view of a surgical system.

Exemplary embodiments of the system and related methods of use disclosed herein are discussed in terms of medical devices for the treatment of musculoskeletal disorders and more particularly, in terms of a surgical system and method for correction of a spine disorder, for example. In various embodiments, the present surgical system includes surgical instruments that allow vertebral manipulation to treat spinal disorders, as described herein, for managing lordosis and/or kyphosis restoration. In various embodiments, the surgical instruments allow for parallel distraction and/or compression of vertebral tissue. In various embodiments, the surgical instruments allow for adjustment of a vertebral body having uneven pedicles in the sagittal plane, for example.

In various embodiments, the present surgical system may be utilized with a method to correct complex spinal deformities. In various embodiments, the present surgical system may be utilized with a method to treat degenerative spinal disorders and/or employed with trans-foraminal lumbar interbody fusion procedures. In various embodiments, the present surgical system is configured for utilization with a sagittal adjusting screw (SAS), a fixed axis screw (FAS) and/or a multi-axial screw (MAS). In various embodiments, the present surgical system comprises a plurality of distractors, such as, for example, at least one distractor disposed along a side of vertebrae to perform a method for treating a spinal disorder such as spondylolisthesis, for example. In various embodiments, the present surgical system comprises a plurality of distractors to treat degenerative spinal disorders, for example, for disposal along a side of vertebrae oriented for distraction, compression, and adjustment of a spacing and/or angle of inclination between vertebrae in the sagittal and/or coronal planes. In various embodiments, the present surgical system includes a micrometric distractor and/or compressor to facilitate angle reduction. For example, various embodiments may provide up to +/−36 angular degrees of lordosis and/or kyphosis restoration.

In various embodiments, the present surgical system includes a surgical instrument connected with an adaptor, which may be utilized with a FAS. In various embodiments, the surgical system includes an angulation module configured for connection with the adaptor and including arms for connection with the extender. In various embodiments, the angulation module is configured for individual angulation of the extenders in a range of +/−20 degrees. In various embodiments, a compressor/distractor may be utilized for parallel distraction. In various embodiments, the surgical instrument includes a compressor/distractor having a reversible ratchet with a neutral, freely moveable position.

In various embodiments, the adaptor is employed with a surgical method including the step of inserting the adaptor with a surgical site and the step of sliding a sleeve along the extender. In various embodiments, the method includes the step of securing the sleeve to the extender. In various embodiments, the method includes the step of connecting a compressor/distractor with the adaptor. In various embodiments, the method includes the step of connecting an angulation module with the adaptor, the compressor/distractor and the extender. In various embodiments, the method includes the step of securing the angulation module, the compressor/distractor and the adaptor with a locking element. In various embodiments, the method includes the step of distracting and/or compressing a posterior ligament. In various embodiments, the method includes the step of actuating a rack and pinion mechanism disposed with the compressor/distractor to facilitate distraction or compression. In various embodiments, the method includes the step of correcting a vertebral angle with the angulation module. In various embodiments, the method includes the step of manually correcting vertebrae using the angulation module to manipulate the extenders, for example, by pivoting the extenders. In various embodiments, the method includes the step of utilizing the angulation module to maintain or fix a corrected vertebrae angle, relative to a compressor/distractor, during compression or distraction with the compressor/distractor.

In various embodiments, the present surgical system includes a surgical instrument connected with an adaptor, which may be utilized with a SAS. In various embodiments, the present surgical system is employed with a surgical technique for the implantation of spinal implants, such as, for example, spinal rods and setscrews. In various embodiments, the spinal rods and setscrews may be implanted percutaneously. In various embodiments, the spinal rods may be reduced relative to a screw head. In various embodiments, the present surgical system is employed with a surgical technique for release of screw head mobility. In various embodiments, the present surgical system is employed with a surgical technique for release of pressure applied during spinal rod reduction. In various embodiments, the present surgical system is employed with a surgical technique for distraction of a posterior ligament. In various embodiments, the surgical system includes manual winglets or a T25 driver that engages a compressor/distractor for performing compression or distraction of vertebrae.

In various embodiments, the present surgical system includes a surgical instrument configured to compress or distract and restore curvature of a spine. In various embodiments, the present surgical system includes instruments and tools for correcting a sagittal deformity and rebalancing a spine of a body. In various embodiments, the present surgical system is employed to treat degenerative deformities of a spine in a sagittal plane, for example, spondylolisthesis and/or degenerative kyphosis. In various embodiments, the present surgical system is employed to treat hyper-kyphosis, flat lumbar back, including disorders that create an unbalance of a body and loss of alignment between body parts. In various embodiments, the present surgical system may be used to reduce scoliosis in the coronal plane by selectively adjusting the compression and/or distraction side at the opposite of the coronal deformity. Furthermore, select vertebra may be de-rotated segmentally during the coronal reduction. In various embodiments, the present surgical system provides a selected amount of correction to apply a selected balance to a spine and provides control and adjustment to the amount of correction in controlled increments. In various embodiments, the present surgical system includes a series of tools and instruments that allow formulation of a type of correction applied and can control the correction stabilization using posterior instrumentation.

In various embodiments, one or all of the components of the surgical system may be disposable, peel-pack, pre-packed sterile devices used with a spinal construct. One or all of the components of the surgical system may be reusable. The surgical system may be configured as a kit with multiple sizes and configurations.

In various embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor, and fractures. In various embodiments, the present disclosure may be employed with other osteal and bone related applications, including those associated with diagnostics and therapeutics. In various embodiments, the disclosed surgical system and methods may be alternatively employed in a surgical treatment with a patient in a prone or supine position, and/or employ various surgical approaches to the spine, including posterior and/or posterior mid-line and in other body regions. The present disclosure may also be alternatively employed with procedures for treating the lumbar, cervical, thoracic, sacral, and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions, or parameters described and/or shown herein, and that the terminology used herein is for the purpose of describing particular embodiments by way of example only and is not intended to be limiting. In various embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other and are not necessarily "superior" and "inferior."

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone, and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are disclosed. Reference is made to the exemplary embodiments of the present disclosure, which are illustrated in the accompanying figures.

The components of surgical system 100 can be fabricated from biologically acceptable materials suitable for medical applications, including metals, synthetic polymers, ceramics, and bone material and/or their composites. For example, the components of surgical system 100, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKELITE™), thermoplastics such as polyaryletherketone (PAEK) including polyetheretherketone (PEEK), polyetherketoneketone PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elasto-mers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 100 may have material composites, including the above materials, to achieve various desired characteristics such as strength, rigidity, elasticity, compliance, biomechanical performance, durability and radiolucency or imaging preference. The components of surgical system 100, individually or collectively, may also be fabricated from a heterogeneous material such as a combination of two or more of the above-described materials. The components of surgical system 100 may be monolithically formed, integrally connected, or include fastening elements and/or instruments, as described herein.

Surgical system 100 may be employed, for example, with a minimally invasive procedure, including percutaneous techniques, mini-open and open surgical techniques to deliver and introduce instrumentation and/or components of spinal constructs at a surgical site within a body of a patient, for example, a section of a spine. In various embodiments, one or more of the components of surgical system 100 may be configured for engagement with spinal constructs attached with vertebrae to manipulate tissue and/or correct a spinal disorder, such as, for example, a sagittal deformity, as described herein. In various embodiments, surgical system 100 may be employed with surgical procedures, such as, for example, corpectomy, discectomy and/or fracture/trauma treatment, scoliosis and spondylolisthesis, and may include fusion and/or fixation that employ implants to restore the mechanical support function of vertebrae. Furthermore, in some instances, surgical system 100 may be referred to as a compressor/distractor 100.

As used herein, it is understood that the term "coronal plane" includes any plane of section in the anatomical position that generally passes vertically through the human body and is generally perpendicular to both the median (or sagittal) plane and the horizontal (or axial or transverse) plane, generally dividing the human body into anterior and posterior sections, and further includes any plane of section in the anatomical position that generally passes vertically through the human body, is generally perpendicular to the horizontal (or axial or transverse) plane, and is generally angularly oriented from the median (or sagittal) plane at an angle of orientation ranging from greater than zero degrees up to and including ninety degrees.

Furthermore, as used herein, it is understood that the term "sagittal plane" includes any plane of section in the anatomical position that generally passes vertically through the human body in the prone position and is generally perpendicular to both the coronal plane and the horizontal (or axial or transverse) plane, generally dividing the human body into left and right sections, and further includes any plane of section in the anatomical position that generally passes vertically through the human body in the prone position, is generally perpendicular to the horizontal (or axial or transverse) plane, and is generally angularly oriented from the coronal plane at an angle of orientation ranging from greater than zero degrees up to and including ninety degrees.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, portions and are also not intended to be limiting. Like terms refer to like elements throughout the description.

Figure 2:
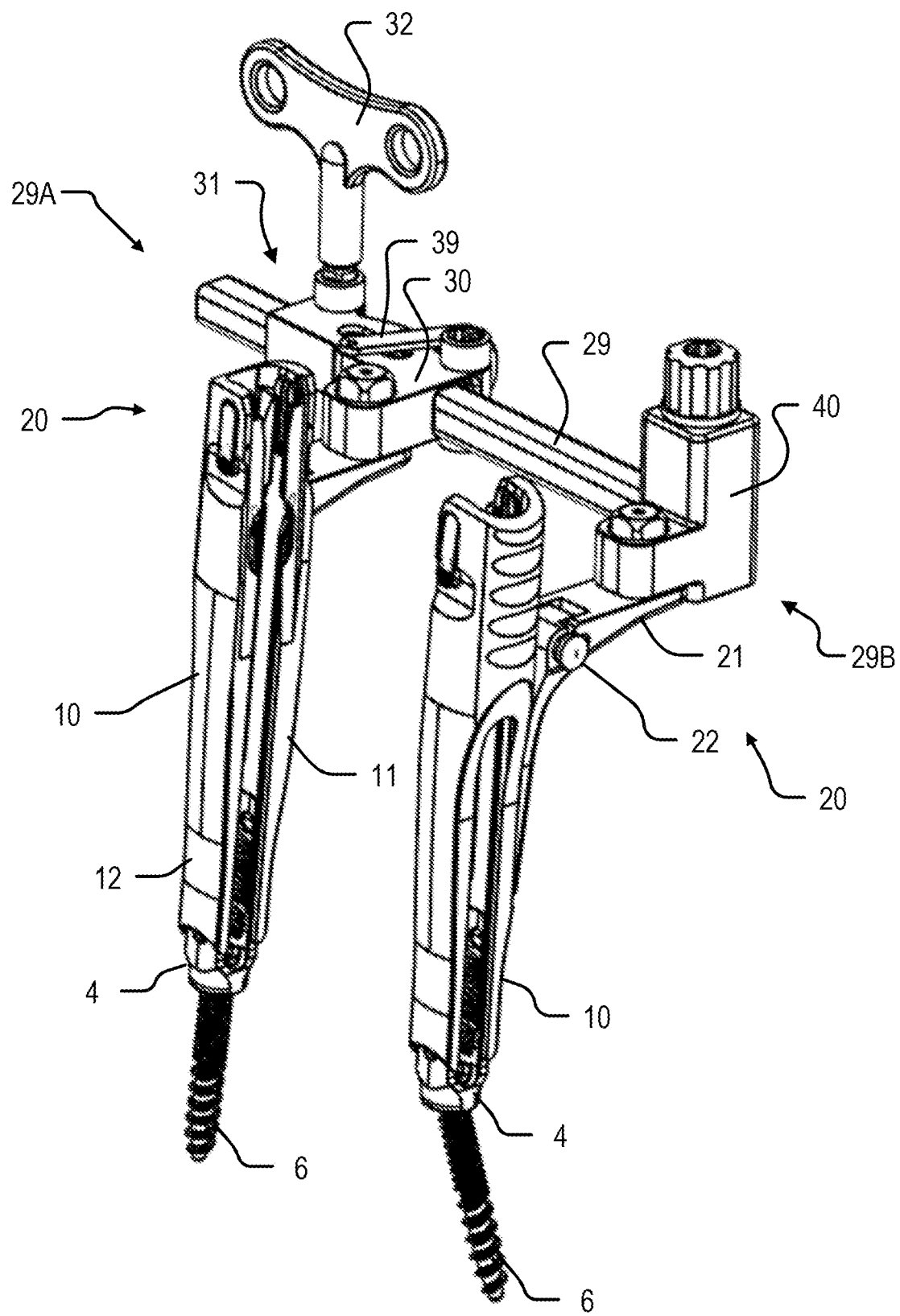
FIG. 2 is a second front perspective view of a surgical system.
Figure 3:
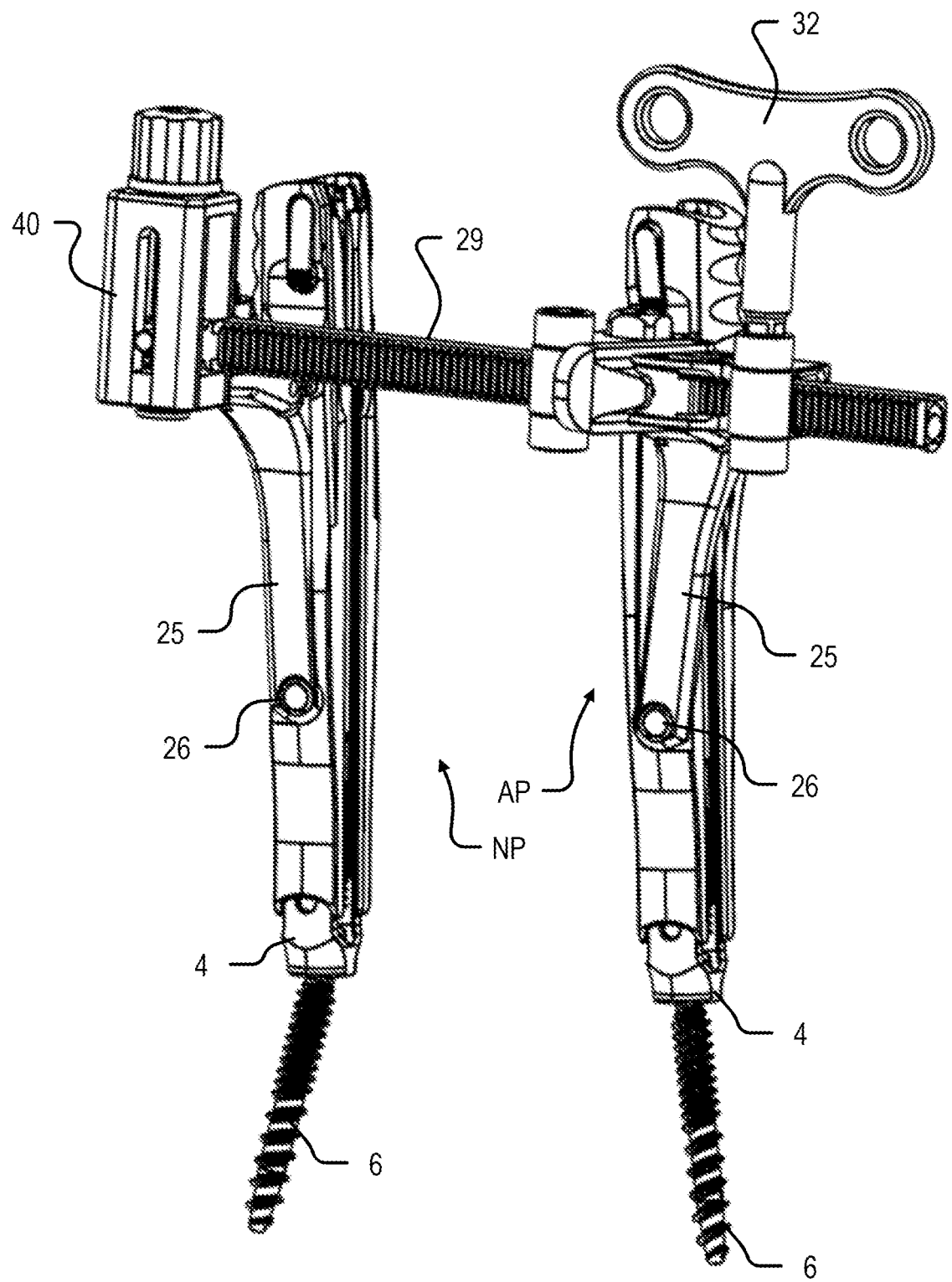
FIG. 3 is a rear perspective view of a surgical system.
Figure 4:
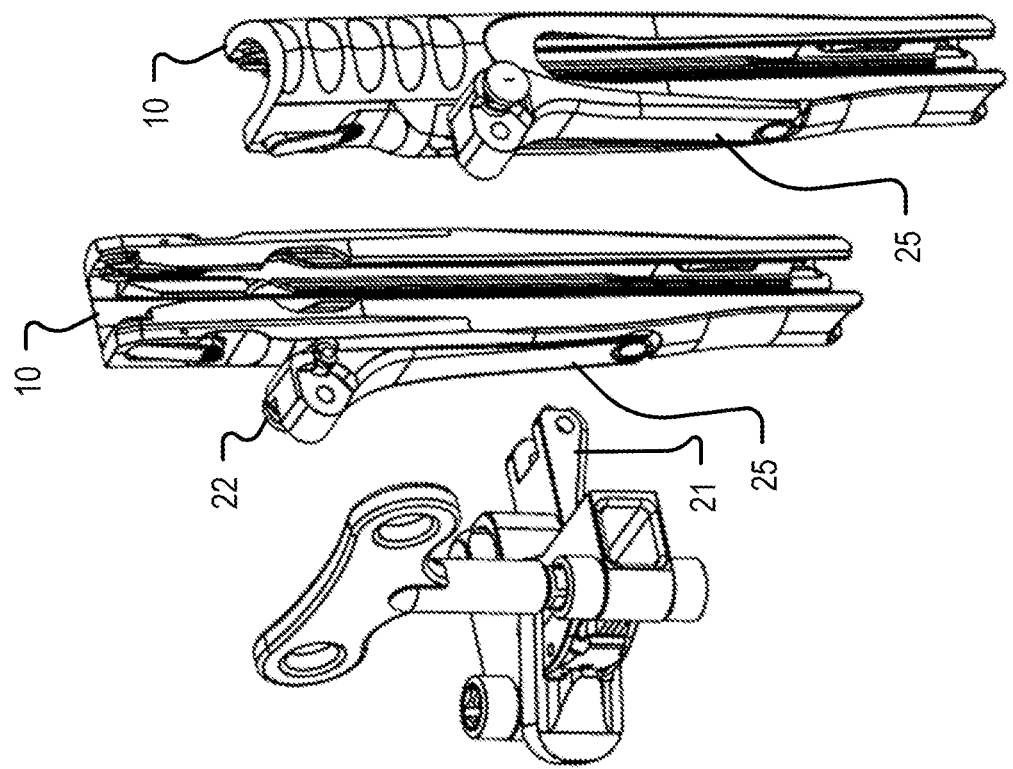
FIG. 4 is an exploded parts view of a surgical system.
Figure 4:
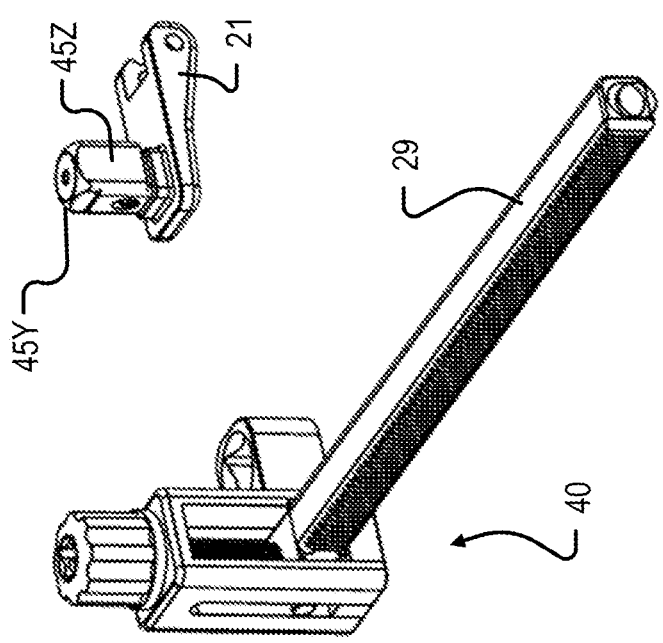

FIGS. 1-3 illustrate various perspective view of a surgical system 100 and FIG. 4 illustrates an exploded parts view of surgical system 100. Various components of surgical system 100 may be combined with any of the surgical components and methods disclosed by U.S. patent application Ser. No. 16/487,057, titled SURGICAL SYSTEM, and filed Aug. 19, 2019, the entire contents of which are incorporated herein by reference, unless the context clearly dictates otherwise. For example, surgical system 100 may include implant supports, such as, for example, connection towers 10 (which may be similar in functionality as extenders disclosed by U.S. patent application Ser. No. 16/487,057).

Referring generally to FIGS. 1-4, connection towers 10 may be engageable with a bone fastener system 2, such as, for example, a fixed axis screw or a multi-axial screw or a fastener element such as a receiver that is coupled to a fixed axis screw or multi-axial screw. In the illustrated embodiment, connection towers 10 are configured to couple to and uncouple from a receiver 4. In various embodiments, receiver 4 may include a lower cavity that is configured to couple to a bone screw and first and second arms that define a U-shaped channel therebetween for receiving a spinal rod (not illustrated). In some embodiments, receiver 4 may be referred to as a tulip head connector that is configured to pop on to bone screw 6 by pushing receiver 4 onto bone screw 6, for example.

In various embodiments, connection towers 10 may include a first leg 11 and a second leg 12 opposite the first leg 11 that extend in a longitudinal direction and define a channel 13 or aperture therebetween. Channel 13 may be configured to allow secondary surgical instruments and or spinal hardware, such as a spinal rod to extend therethrough (not illustrated), for example. As will be explained in further detail below, connection towers 10 may be independently manipulable, to provide counter-torque for various maneuvers and manipulation of vertebrae during a surgical treatment, for example, to distract and/or compress, pull and/or push, raise and/or lower, twist, and/or otherwise align vertebrae.

Figure 6:
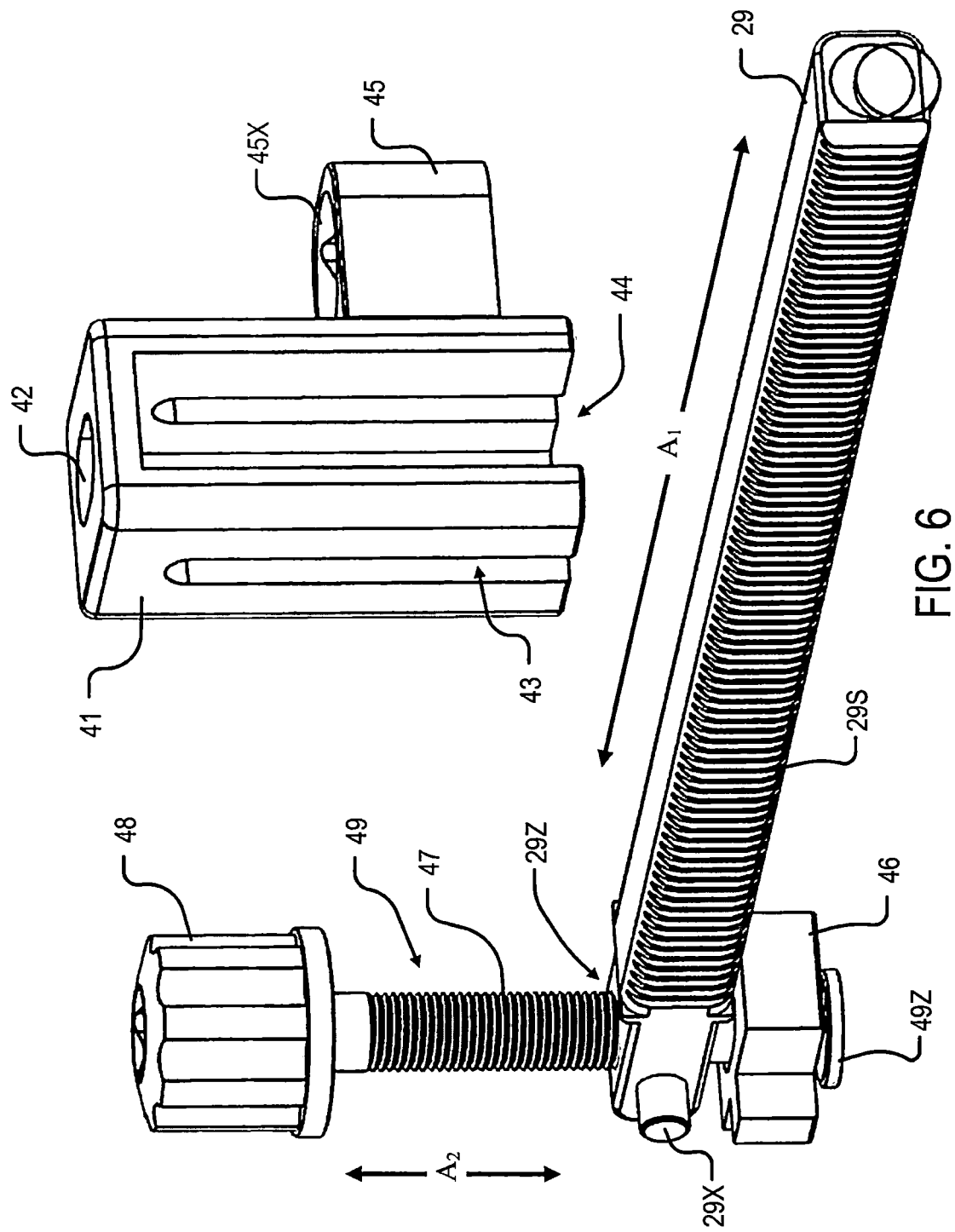
FIG. 6 is an exploded parts view of an adjustment mechanism.

In various embodiments, surgical tool 100 may include a rack 29 extending in a first direction, e.g., a longitudinal direction between a first end 29A and a second end 29B (see FIG. 6). Additionally, a spline portion 29S may extend along a portion of rack 29 between the first end 29A and second end 29B. Rack 29 may be configured to connect to adjacent connection towers 10 and facilitate relative motion of connection towers 10 along a longitudinal axis $A_1$ in the longitudinal direction (see FIG. 6). For example, rack 29 may be configured to connect to adjacent connection towers 10 and facilitate relative motion of connection towers 10 along a longitudinal axis $A_1$.

In the example embodiment, a first connection tower 10 may be coupled to a sliding body 30 that may facilitate motion of first connection tower 10 along longitudinal axis $A_1$. Sliding body 30 may include a ratchet mechanism 31 including a turnkey 32 (or actuator 32) that is engageable in a bi-directional and/or two-way ratchet configuration with splines 29S of rack 29. In some embodiments, ratchet mechanism 31 may include various gears that may be toothed however ratchet mechanism 31 need not necessarily include teeth and/or gears. In various embodiments, turnkey 32 includes a gear surface engageable with splines 29S of rack 29 to axially and/or incrementally translate sliding body 30 and facilitate distraction and/or compression, as described herein. In some embodiments, ratchet mechanism 31 may optionally include a pawl 39 that allows for incremental translation of sliding body 30 in a first direction relative to rack 29 while also preventing axial translation of sliding body 30 in an opposite direction, for example. As such, distraction of vertebral tissue connected with connection towers 10 via bone fastener 2 can be performed. In some embodiments, and depending on orientation, ratchet mechanism 31 may be configured to move sliding body portion 30 (and first connection tower 10) back and forth along the longitudinal axis $A_1$ which corresponds to the cranial/caudal directions of the coronal plane (see orientation of surgical device 100 in FIGS. 7-8 and reference diagram FIG. 12). As such, ratchet mechanism 31 may be referred to as a "Coronal Plane Actuator" in some embodiments.

In the example embodiment, an adjustment mechanism 40 may be coupled to rack 29 adjacent second end 29B. In various embodiments, adjustment mechanism 40 may be constrained from movement in the longitudinal direction along axis $A_1$. Moreover, adjustment mechanism 40 may be coupled to a second adjustment tower 10 (opposite a first adjustment tower 10 that is coupled to sliding body 30) and be configured to raise and lower second adjustment tower 10 in a vertical direction along a vertical axis $A_2$ (see FIG. 6). In some embodiments, and depending on orientation, connection tower 10 may be configured to raise and lower second adjustment tower 10 in a vertical direction corresponding to the ventral/dorsal directions of the sagittal plane (see orientation of surgical device 100 in FIGS. 7-8 and reference diagram FIG. 12). As such, adjustment mechanism 40 may be referred to as a "Sagittal Plane Actuator" in some embodiments. Further details regarding adjustment mechanism 40 will be explained in detail below with reference to FIGS. 5-6.

In the example embodiment, sliding body 30 and adjustment mechanism 40 may each be coupled to an angulation assembly 20. Each angulation assembly 20 may, in turn, be coupled to a corresponding connection tower 10. In various embodiments, angulation assembly 20 may include a first pivotal linkage 21 (may also be referred to as a transverse linkage assembly) that allows pivoting of a corresponding connection tower 10 about a first pivot point 22 (may also be referred to as a transverse pivot point) such as a pin or hinge. In various embodiments, first pivot point 22 may be coupled to a second pivotal linkage 25 or alternatively may be directly connected to a connection tower 10 (not illustrated). In the example embodiment, first pivotal linkage 21 may allow connection tower 10 to pivot about first pivot point to an angled position AP (see FIG. 1) within an angular range of about +/−0 degrees to about 20 degrees from a normal position NP (see FIG. 1) in which the corresponding connection tower 10 extends vertically and substantially perpendicular to a main extension direction of rack 29. In this way, and depending on orientation, first pivotal linkage 21 may allow for pivoting of a corresponding connection tower 10 along the transverse plane (see orientation of surgical device 100 in FIGS. 7-8 and reference diagram FIG. 12).

In various embodiments, angulation assembly 20 may include a second pivotal linkage 25 (may also be referred to as a coronal linkage assembly) that allows pivoting of a corresponding connection tower 10 about a second pivot point 26 (may also be referred to as a coronal pivot point) such as a pin or hinge. In the example embodiment, second pivotal linkage 25 may allow connection tower 10 to pivot about second pivot point to an angled position AP (see FIG. 3) within an angular range of about +/−20 degrees from a normal position NP (see FIG. 3) in which the corresponding connection tower 10 extends substantially perpendicular to a main extension direction of rack 29 (compare NP to AP in FIG. 3).

Figure 7:
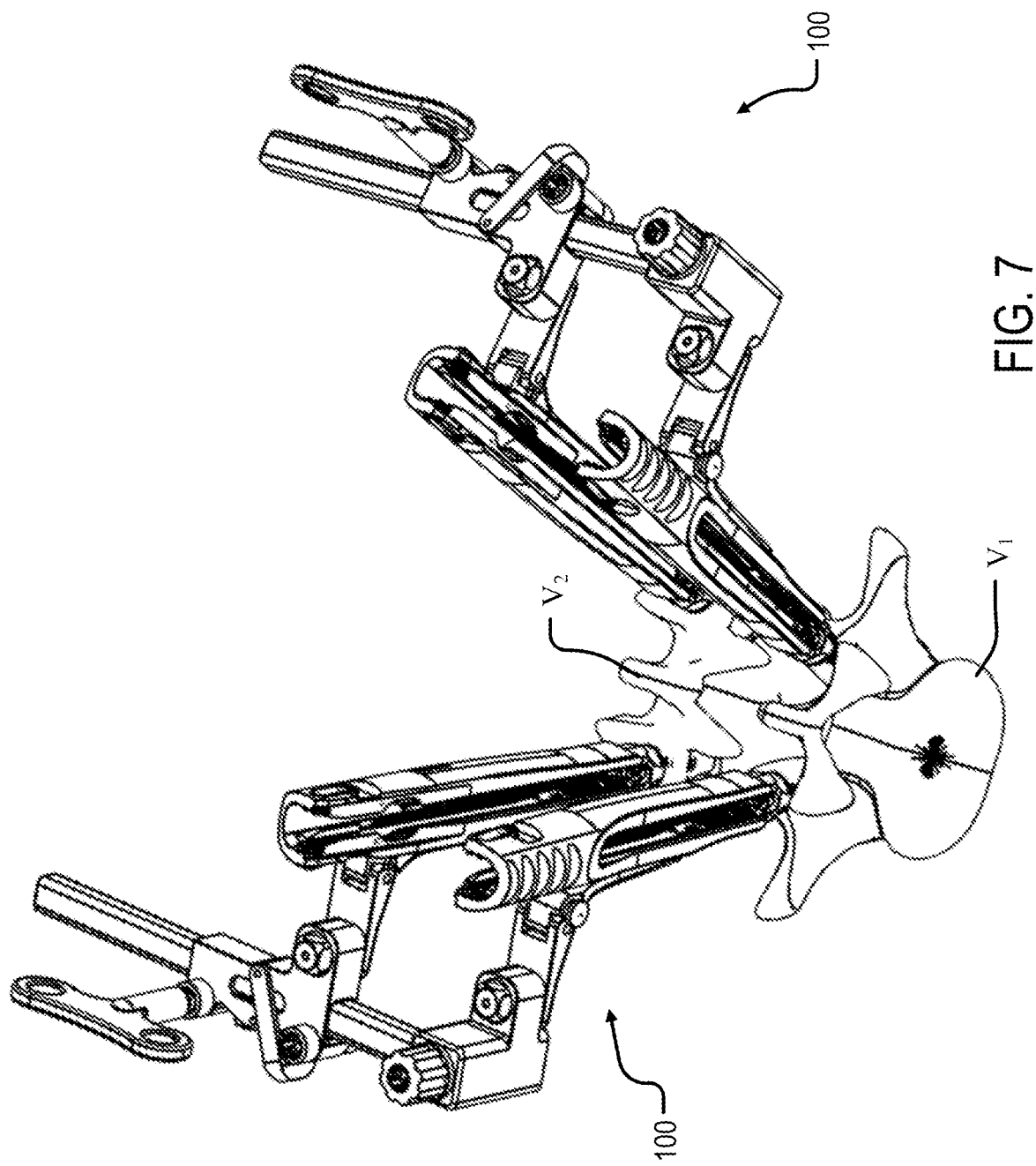
FIG. 7 is a first perspective view of a first surgical system and a second surgical system being used to treat the spine.
Figure 8:
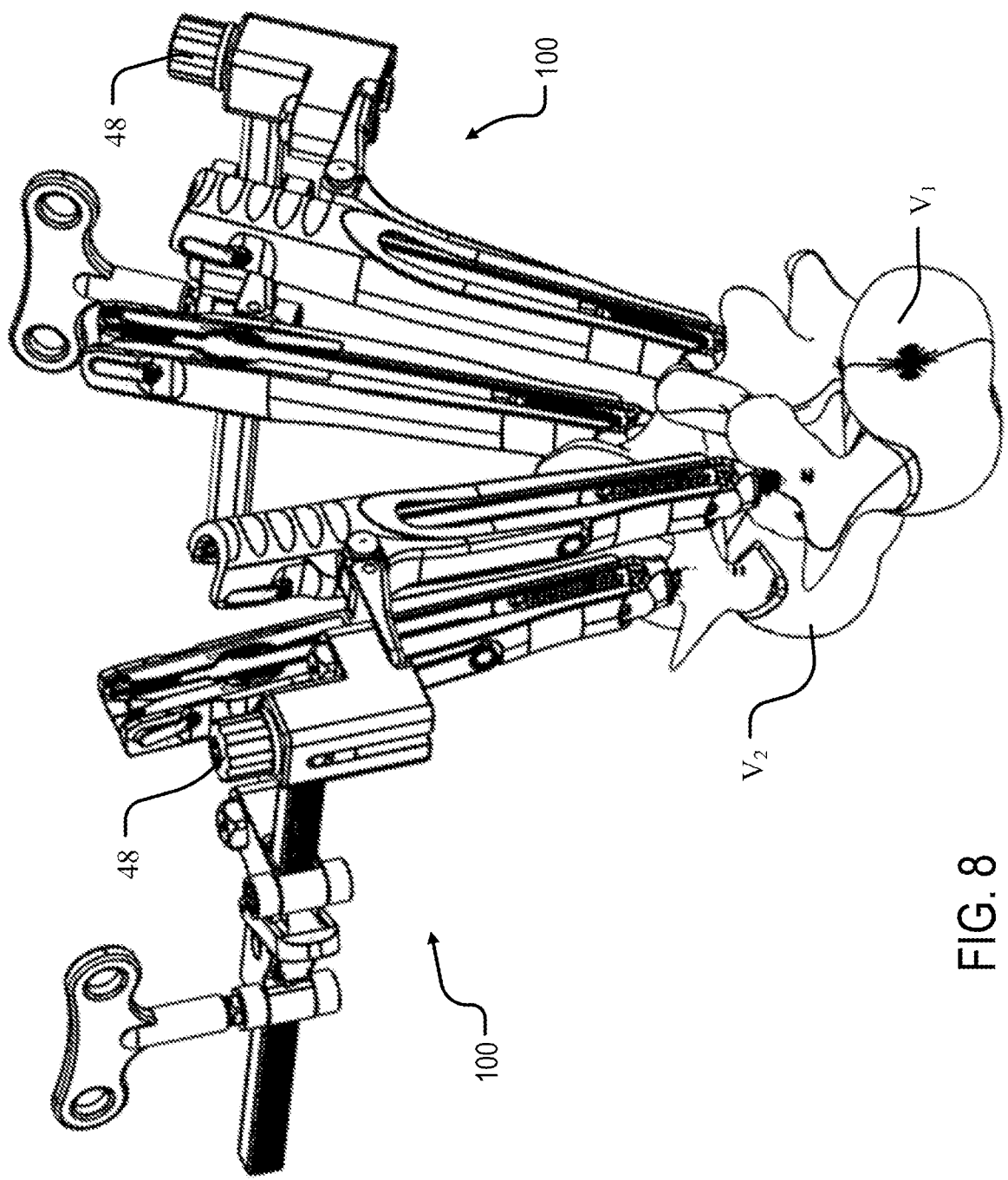
FIG. 8 is a second perspective view of a first surgical system and a second surgical system being used to treat the spine.
Figure 12:
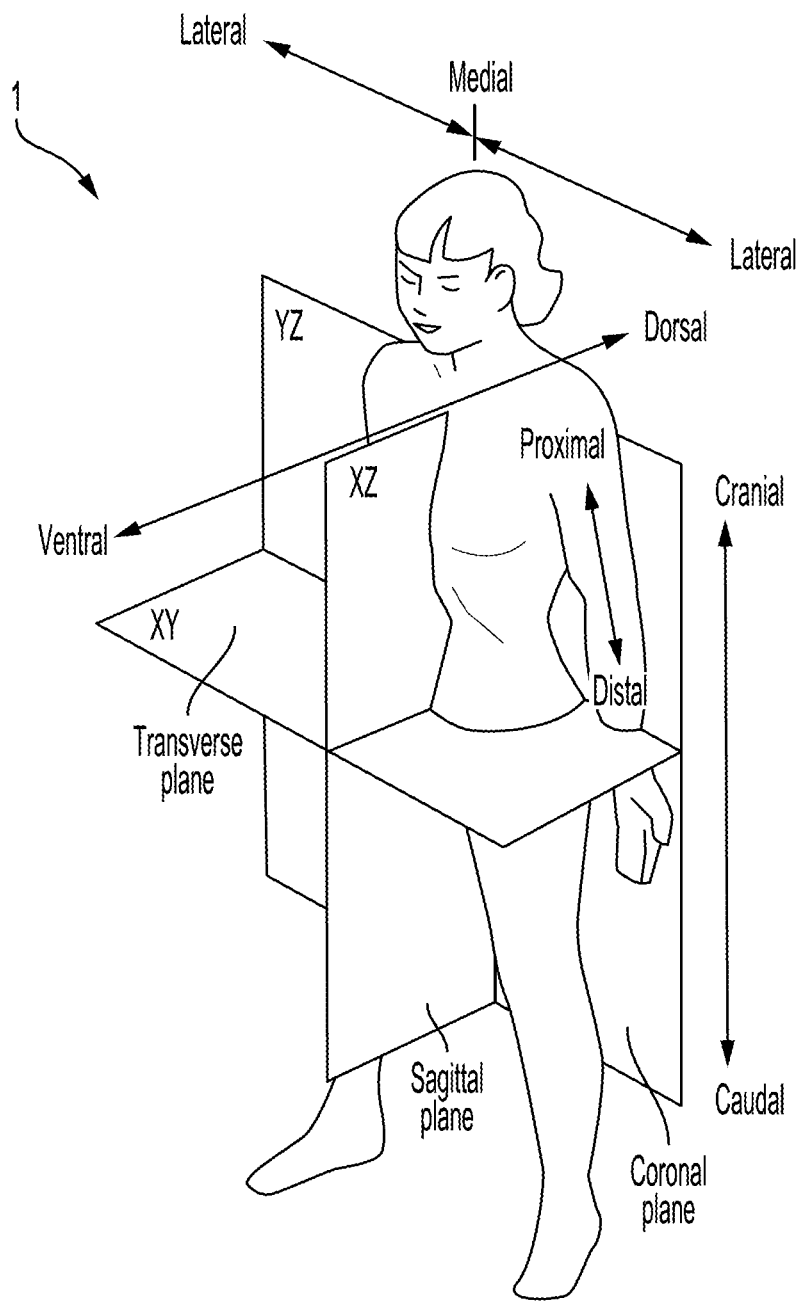
FIG. 12 is a reference diagram explaining various planes and directions in relation to the human body.

In this way, and depending on orientation, first pivotal linkage 21 may allow for pivoting of a corresponding connection tower 10 along the coronal plane (see orientation of surgical device 100 in FIGS. 7-8 and reference diagram FIG. 12). In various embodiments, second pivot point 26 may be secured to an intermediate and/or adjacent a medial portion of connection tower 10.

Figure 5:
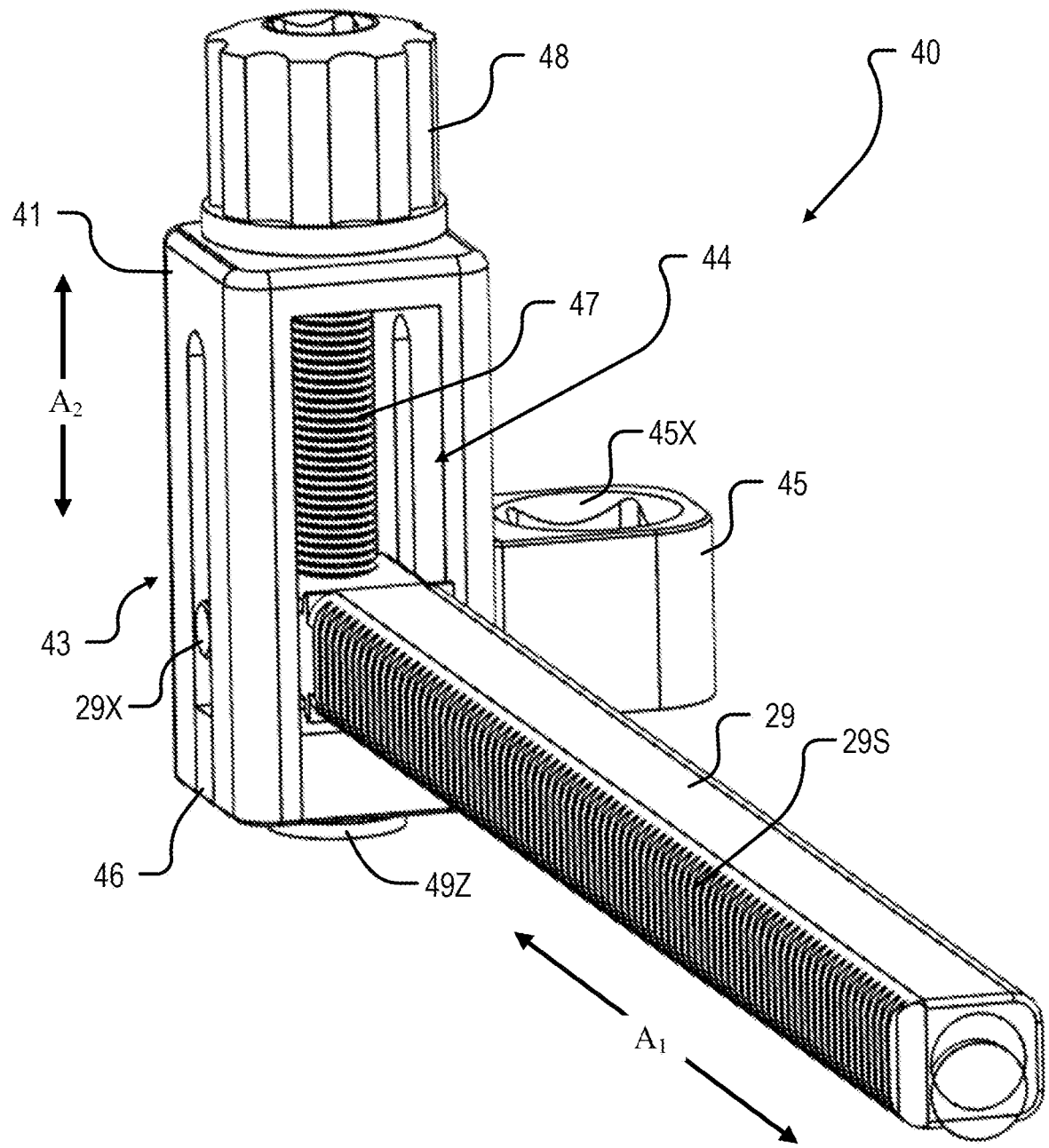
FIG. 5 is a perspective view of an adjustment mechanism.

Referring generally to FIGS. 5-6, adjustment mechanism 40 is shown. As disclosed above, adjustment mechanism 40 may be configured for moving a corresponding connection tower 10 in along a vertical axis $A_2$ (see FIG. 6) corresponding to the ventral/dorsal directions of the sagittal plane (see orientation of surgical device 100 in FIGS. 7-8 and reference diagram FIG. 12). Adjustment mechanism 40 may include a body portion 41 having a rectangular shape including an arm 45 extending therefrom for coupling with angulation assembly 20, for example. In various embodiments, arm 45 may include a coupling aperture 45X configured to mate with a coupling protrusion 45Z (see FIG. 4). In the example embodiment, coupling aperture 45X is substantially rectangular and includes curved indents and/or chamfers at the corners thereof corresponding to the curved indents and/or chamfers at the corners of coupling protrusion 45Y. At least one advantage of this configuration may be that the rectangular shape and chamfered/indented corners of the coupling aperture 45X and coupling protrusion 45Y allow for minor relative angulation of an attached angulation assembly about +/−5 degrees in all directions (in addition to the angular ranges explained above with respect to the first pivotal linkage 21 and second pivotal linkage 25).

In the example embodiment, body portion 41 may include an aperture 42 at an upper end thereof of which an adjustment screw 49 may extend therethrough. Adjustment screw 49 may include a knob portion 48 at a first end, a stop feature 49Z at a second end, and a threaded body portion 47 therebetween. Additionally, adjustment screw 49 may extend through a threaded aperture 29Z adjacent second end 29B of rack 29. Furthermore, rack 29 may include a first pivot point in the form of a protrusion 29X. In at least some embodiments first protrusion 29X may take the shape of a circular pin and be disposed on the same side surface as splines 29S such that it may form a pivotable connection point between rack 29 and second slot 43 of body portion 41.

As seen best in FIG. 5, a portion of rack 29 may be disposed within a first slot 44 along a first face of body portion 41 and protrusion 29X may be disposed within a second slot 43 along a second face of body portion 41. Additionally, a support block 46 may have a cross like shape in which a first protrusion is disposed within the first slot 44 and a second protrusion is disposed within the second slot 43 while the stop feature 49Z constrains the aforementioned components in place. In this way, adjustment mechanism 40 may be constrained from moving in the longitudinal direction along axis $A_1$ while permitting relative motion in the vertical direction along axis $A_2$. In operation, an end user (such as a surgeon) may rotate adjustment screw 49 by turning knob portion 48 thereby causing relative motion of adjustment mechanism 40 relative to rack 29. For example, rotation of adjustment screw 49 may facilitate and/or cause motion of an adjacent connection tower 10 in a vertical direction corresponding to the ventral/dorsal directions of the sagittal plane (see orientation of surgical device 100 in FIGS. 7-8 and reference diagram FIG. 12). In various embodiments, adjustment screw 49 may allow about +/−30 mm of adjustment in the vertical direction. In at least one embodiment, turning knob 48 may allow about +/−20 mm of adjustment in the vertical direction. Additionally, in various embodiments, slot 42 may take an oblong shape and stop feature 49Z may take a spherical shape such that a contact point between stop feature 49Z and support block 46 can accommodate a position change of adjustment screw 49 and/or turning knob 48, for example. At least one advantage of this configuration may be that rack 29 may allow for an additional +/−10° of angle adjustment around protrusion 29x relative to the sagittal plane.

Figure 9:
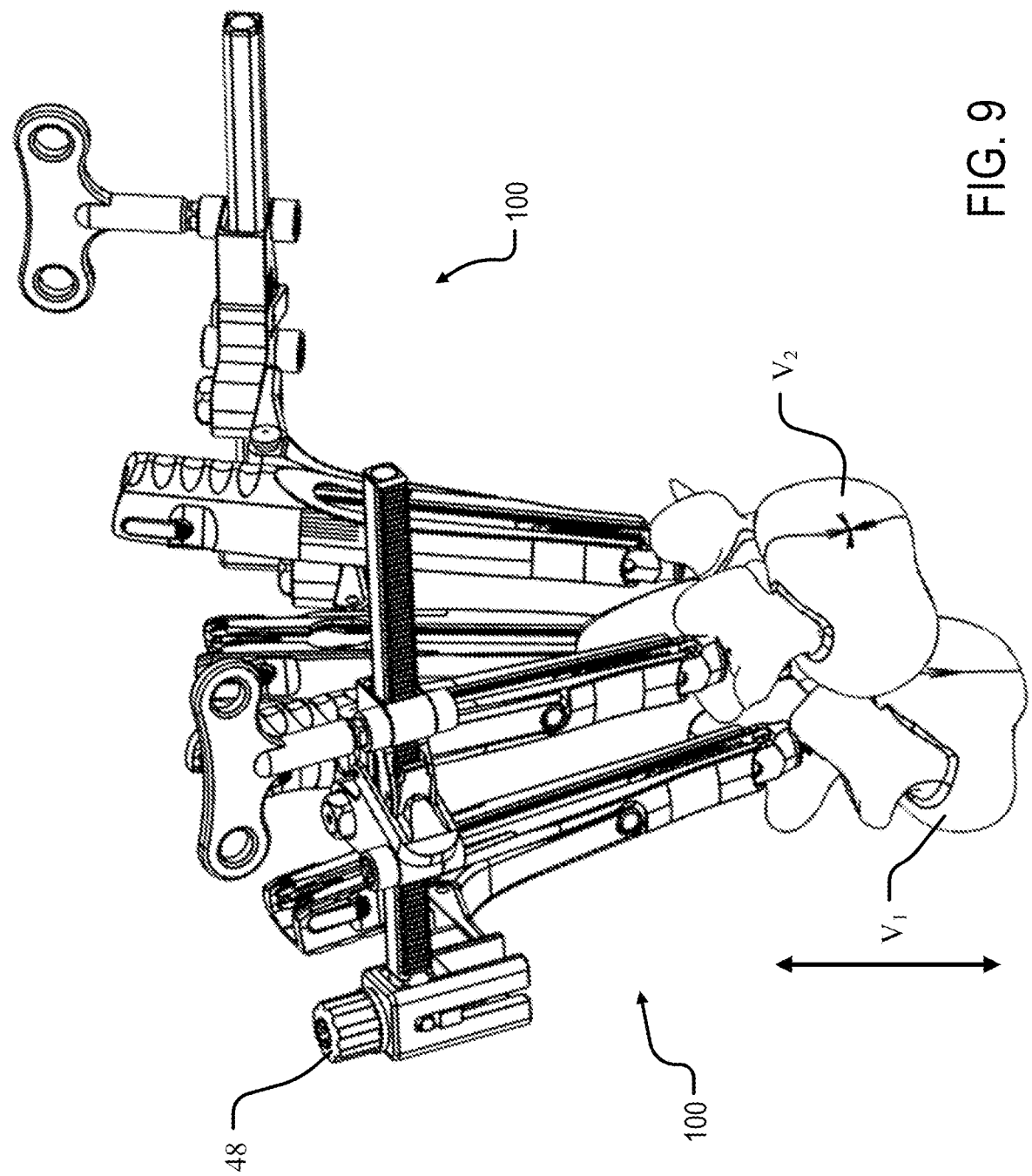
FIG. 9 is a third perspective view of a first surgical system and a second surgical system being used to treat the spine.
Figure 10:
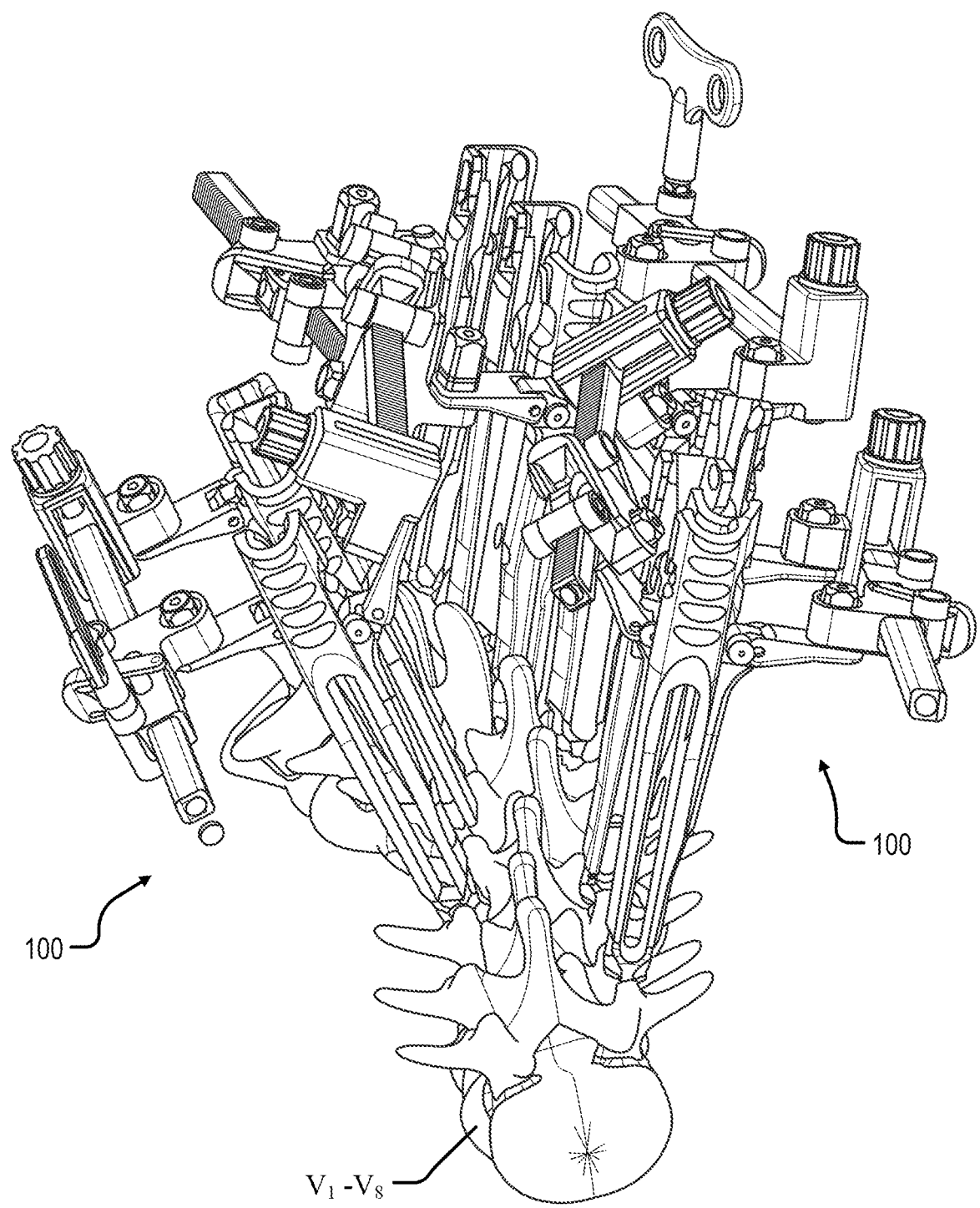
FIG. 10 is a first perspective view of a plurality of surgical systems being used to treat the spine.
Figure 11:
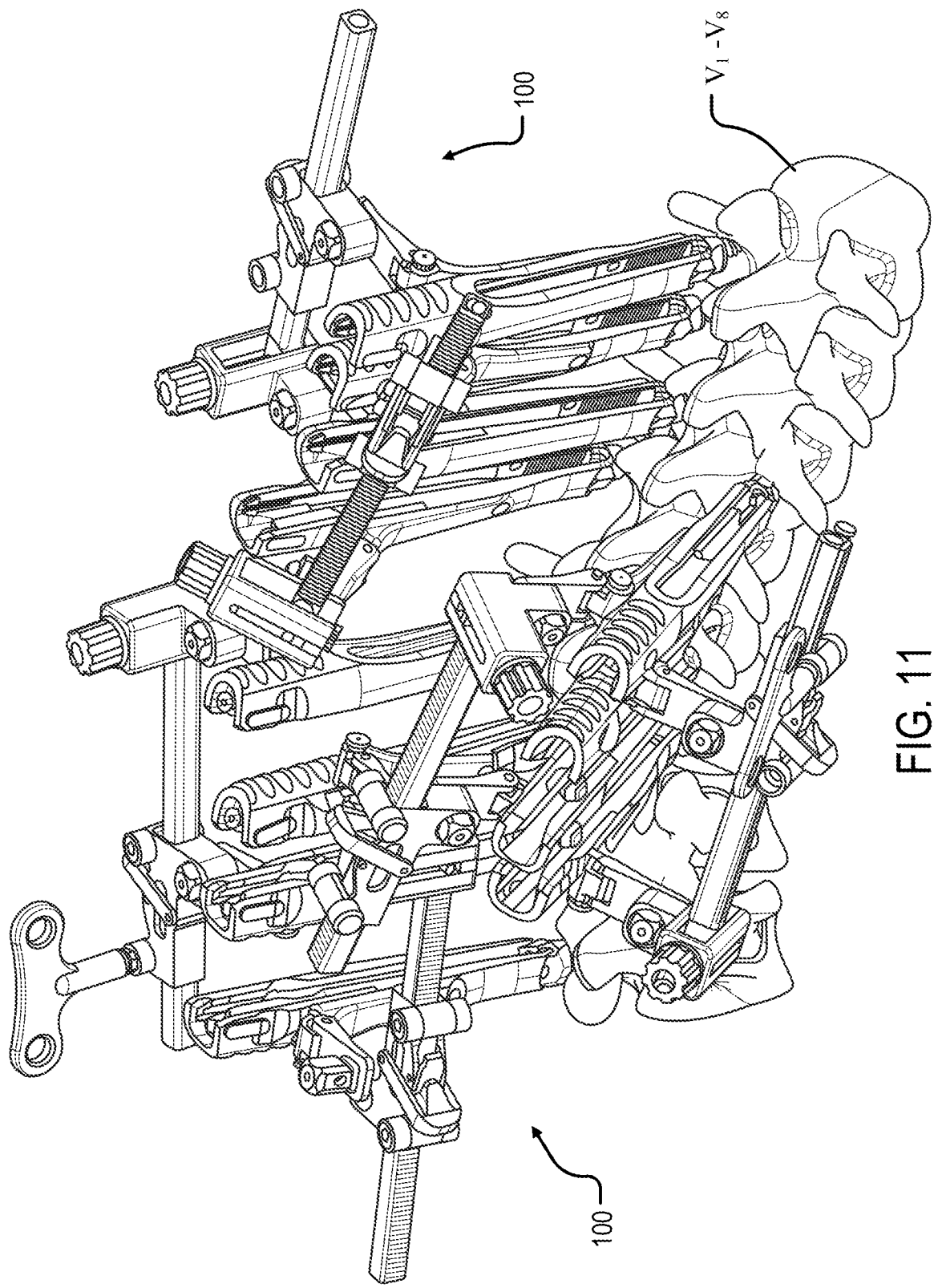
FIG. 11 is a second perspective view of a plurality of surgical systems being used to treat the spine.

Referring generally to FIGS. 7-11, various methods of operation of a surgical system 100 and/or a plurality of surgical systems 100 will be disclosed. FIGS. 7-9 illustrate a first and second surgical system 100 being used to treat a spondylolisthesis condition and FIGS. 10-11 illustrate a plurality of surgical systems 100 being used to treat a scoliosis condition. Although not illustrated specifically, surgical system 100 also may be employed with surgical procedures, such as, for example, discectomy, laminectomy, fusion, laminotomy, laminectomy, nerve root retraction, foraminotomy, facetectomy, decompression, spinal nucleus or disc replacement and bone graft and implantable prosthetics including plates, rods, and bone engaging fasteners. Those with skill in the art will readily appreciate how embodiments in accordance with the principles of this disclosure may be broadly employed for treatment of a spine of a human patient or a non-human patient and/or other boney anatomy.

FIGS. 7-9 illustrate use of an example embodiment to correct spondylolisthesis of a vertebral segment between a first vertebra $V_1$ and a second vertebra $V_2$ in which the pedicle portions of vertebra $V_1$, $V_2$ are uneven, e.g., with a patient in a prone position the pedicle portions of $V_1$, $V_2$ are disposed at different relative heights from an operating table. In a first step, a surgeon may obtain access to a surgical site including vertebrae V in any appropriate manner, such as through incision and retraction of tissues. In various embodiments, surgical system 100 may be used in any existing surgical method or technique including open surgery, mini open surgery, minimally invasive surgery, and percutaneous surgical implantation, whereby vertebrae $V_1$, $V_2$ may be accessed through a mini-incision, cannula, or sleeve to thereby provide a passageway to the target area. In various embodiments, an incision may be made in the body of a patient and a cutting instrument (not shown) may create a surgical pathway for implantation of select components of surgical system 100. In at least some embodiments, a preparation instrument (not shown) may optionally be employed to prepare and/or clean various surfaces of vertebrae $V_1$, $V_2$, as well as for aspiration and irrigation of a surgical region, on an as needed basis. In a second step, a surgeon may install a bone fastener a bone fastener, e.g., bone fastener system 2 to select portions of the human spine. In at least some implementations, pilot holes or the like may be drilled in non-damaged or non-diseased areas of vertebra $V_1$, $V_2$ for receiving a bone fastener, e.g., bone fastener system 2. In the example embodiment, a surgeon has installed two bone screws 6 in the opposite pedicle portions of a first vertebra $V_1$, and has installed two bone screws 6 in the opposite pedicle portions of a second vertebra $V_2$.

In a third step, a surgeon may connect a corresponding connection tower 10 to each bone fastener system 2. For example, a surgeon may utilize a first system 100 by connecting a first connection tower 10 to a first bone fastener system 2 of vertebra $V_1$ and connect the second connection tower 10 to a second bone fastener system 2 of vertebra $V_2$. Similarly, a surgeon my utilize a second system 100 by connecting a third connection tower 10 to a third bone fastener system 2 of vertebra $V_1$ and connect the fourth connection tower 10 to a fourth bone fastener system 2 of vertebra $V_2$. In this way, each system 100 uses one of the connection towers 10 to connect to a pedicle portion of first vertebra $V_1$ and utilizes the other connection tower 10 to connect to a pedicle portion of a second vertebra. For example still, a first system 100 may connect to the left pedicle portions of vertebra $V_1$, $V_2$ and a second system 100 may connect to the right pedicle portions of vertebra $V_1$, $V_2$. Furthermore, in a fourth step, a surgeon may raise and/or lower a corresponding connection tower via adjustment mechanism 40 on an as needed basis according to the patient specific anatomy to facilitate coupling to any of the various bone fastener systems 2.

In a fifth step, and depending on the patient specific conditions, a surgeon may distract the disc space between vertebra $V_1$, $V_2$ by rotating actuator key 32 of ratchet mechanism 31. In doing so, sliding body portion 30 may move away from adjustment mechanism 40 along longitudinal axis A1 as explained above. Accordingly, the disc space between vertebra $V_1$, $V_2$ may become enlarged and/or distracted. Furthermore, those with skill in the art will readily appreciate that a surgeon may selectively cause distraction of the disc space adjacent to the left pedicles and/or adjacent to the right pedicles depending on which corresponding system 100 is utilized. Likewise, if a surgeon determines that the disc space disc space adjacent to the left pedicles and adjacent to the right pedicles should be distracted a surgeon can rotate each actuator key 32.

In a sixth step, a surgeon may raise and/or lower a vertebra $V_1$, $V_2$ on an as needed basis by rotating knob portion 48 and the adjustment screw of adjustment mechanism 40. With reference to FIG. 9, a surgeon may rotate a first knob 48 and adjustment screw 49 of a first system 100 in order to raise a corresponding pedicle portion of vertebra $V_1$ in the sagittal plane such that the corresponding pedicle portion may be aligned (or better aligned) with the natural position of vertebra $V_2$. If needed, a surgeon may repeat this step by rotating a second knob 48 and adjustment screw 49 of a second system 100 in order to raise a corresponding pedicle portion of vertebra $V_1$ in the sagittal plane such that the corresponding pedicle portion may be aligned (or better aligned) with the natural position of vertebra $V_2$.

In a seventh step, a surgeon may optionally further manipulate a position of vertebra $V_1$, $V_2$ in the transverse plane via angulation of first linkage assembly 21 of angulation assembly 20. In a seventh step, a surgeon may optionally further manipulate a position of vertebra $V_1$, $V_2$ in the sagittal plane via second linkage assembly 25. It shall be appreciated that manipulating vertebra $V_1$, $V_2$ during steps three through seven may be relatively safe and/or smooth on account of angulation assembly 20 allowing for pivoting in the transverse and sagittal planes. In an eighth step, a surgeon may optionally repeat any of the aforementioned steps to safely manipulate vertebra $V_1$, $V_2$ until a target alignment is achieved. For example, a surgeon may perform any of the aforementioned steps incrementally to control the distraction of disc space and/or the adjustment of vertebra $V_1$, $V_2$. In a ninth optional step, a surgeon may optionally install an interbody implant between adjacent vertebra $V_1$, $V_2$ to facilitate a fusion process. In a tenth optional step, a surgeon may optionally install a spinal rod that connects adjacent receivers 4 to maintain the alignment obtained via performance of the aforementioned steps.

FIGS. 10-11 illustrate use of an example device to correct scoliosis of a vertebral segment of a human spine including vertebra $V_1$ through Vs. In this example, a surgeon may be correcting the curvature of the spine by iteratively manipulating a sub-portion of vertebra $V_1$-$V_8$. In some embodiments, correction of scoliosis may be achieved by compressing a respective vertebra $V_1$-$V_8$ at the apex of the curve of the corresponding vertebra and distracting on the other side of the corresponding vertebra on a segment by segment basis. This procedure may yield the objective result of straightening out the spine by creating a wedge of the disc space coronally such that the target segment of the spine becomes straight.

This surgical procedure may include a plurality of surgical systems 100 selectively engaged with and/or coupled to select pedicle portions of select vertebra $V_1$-$V_8$. Additionally, this surgical procedure may include any of steps one through eight as explained above with the end purpose of restoring and/or correcting the curvature of the spine. Similarly, a surgeon may optionally perform step nine to install an interbody implant to facilitate a fusion process and/or perform step ten to connect adjacent receivers 4 to maintain the spinal alignment obtained via performance of the preceding steps.

Upon completion of the procedures described herein, the surgical instruments, assemblies, and non-implanted components of surgical system 100 may be removed and the incision(s) may be closed. In various embodiments, the use of surgical navigation, microsurgical and image guided technologies may be employed to access, view and repair spinal deterioration or damage, with the aid of surgical system 100. In various embodiments, surgical system 100 may include one or a plurality of plates, connectors and/or bone fasteners for use with a single vertebral level (see FIGS. 7-9) or a plurality of vertebral levels (see FIGS. 10-11). FIG. 12 is a reference diagram explaining various planes and directions in relation to the human body.

It will be understood that various modifications may be made to the embodiments disclosed herein. There-fore, the above description should not be construed as limiting, but merely as exemplification of the various embodiments. Those skilled in the art will envision other modifications within the scope and spirit of the claims appended hereto.

The term "about" as used herein may be applied to modify any quantitative representation which could permissibly vary without resulting in a change in the basic function to which it is related. For example, the adjustment screw 49 may allow +/−30 mm of adjustment in the vertical direction as disclosed herein but may permissibly have a variation of several digits, such as 5 mm, yet remain within the scope of the invention so long as the function of the adjustment screw is not materially altered.

What is claimed is:

1. A surgical system for adjusting a segment of a spine, comprising:
   a rack arm extending in a longitudinal direction from a first end to a second end, the rack arm including a spline portion;
   a sliding body including a ratcheting mechanism having a first actuator and a pawl selectively engageable with the spline portion of the rack arm, the first actuator comprising a rotatable gear meshed with the spline portion configured to translate the sliding body along the rack arm in the longitudinal direction;
   a first connection tower extending along a first axis transverse to the longitudinal direction and being coupled to the rack arm;
   a second connection tower extending along a second axis transverse to the longitudinal direction and being coupled to the sliding body; and
   an adjustment mechanism configured to facilitate movement of the first connection tower along the first axis, the adjustment mechanism comprising a body portion, at least two elongate slots formed through respective sidewalls of the body portion, and an aperture formed in an upper wall of the body portion that is opposed from a lower wall of the body portion; and
   a second actuator including a threaded screw that extends through the aperture formed in the upper wall of the body portion and is configured to facilitate an adjustment of a location of the first connection tower along the first axis;
   wherein the second end of the rack arm extends through a first slot of the at least two elongate slots formed through the sidewalls of the body portion, and a pivot structure protruding out from the second end of the rack arm extends through a second slot of the at least two elongate slots formed through the sidewalls of the body portion.

2. The system of claim 1, wherein the second actuator is configured to raise and lower the first connection tower in a sagittal plane.

3. The system of claim 1,
   wherein the pivot structure of the rack arm is movably disposed within the second slot to provide a pivoting point for the rack arm in the sagittal plane,
   wherein the first connection tower is constrained from moving in the longitudinal direction, and
   wherein the second actuator is further configured as a freely rotatable actuator that is configured to facilitate movement of the pivot structure within the second slot in the sagittal plane.

4. The system of claim 1, wherein at least one of the first connection tower and the second connection tower is coupled to the rack arm via an angulation assembly.

5. The system of claim 4, wherein each angulation assembly includes a first linkage assembly configured to facilitate pivoting in a transverse plane.

6. The system of claim 5, wherein each angulation assembly includes a second linkage assembly configured to facilitate pivoting in a coronal plane.

7. The system of claim 1, wherein the first connection tower is configured to distract a disc space between adjacent vertebrae in a coronal plane.

8. The system of claim 1, wherein at least one of the first connection tower and the second connection tower is configured to couple to a bone fastener system.

9. The system of claim 1, wherein at least one of the first connection tower and the second connection tower is configured to couple to a multi-axial bone fastener system.

10. The system of claim 1, wherein at least one of the first connection tower and the second connection tower is configured to couple to receiver of a bone fastener system.

11. A surgical system for adjusting a segment of a spine, comprising:
    a ratchet comprising a rack arm extending in a longitudinal direction and a sliding body movable along a length of the rack arm in the longitudinal direction, the sliding body comprising a pawl engageable with the rack arm;
    an adjustment mechanism comprising a body portion, at least two elongate slots formed through respective sidewalls of the body portion, an aperture formed in an upper wall of the body portion that is opposed from a lower wall of the body portion, and a threaded actuator extending through the aperture formed in the upper wall;
    a first angulation assembly coupled to the adjustment mechanism;
    a second angulation assembly coupled to the sliding body;
    a first connection tower configured to couple to a first bone fastener, the first connection tower extending along a first axis transverse to the longitudinal direction and being pivotably coupled to the first angulation assembly; and a second connection tower configured to couple to a second bone fastener, the second connection tower extending along a second axis transverse to the longitudinal direction and being pivotably coupled to the sliding body;

wherein the threaded actuator is configured to translate the first connection tower relative to the rack arm in a sagittal plane;

wherein an end of the rack arm extends through a first slot of the at least two elongate slots formed through the sidewalls of the body portion, and a pivot structure protruding out from the second end of the rack arm extends through a second slot of the at least two elongate slots formed through the sidewalls of the body portion.

12. The surgical system of claim 11, further comprising a rotatable actuator including a plurality of teeth that are engageable with correspondingly sized teeth of a spline portion of the rack arm, the rotatable actuator being configured to move the sliding body forward and backward along the rack arm upon rotation of a rotatable key.

13. The surgical system of claim 12, wherein:
the pivot structure of the rack arm is movably disposed within the second slot; and
the end of the rack arm is movably disposed within the first slot.

14. The surgical system of claim 13, wherein the adjustment mechanism is constrained from moving in the longitudinal direction.

15. The surgical system of claim 13, wherein the threaded actuator is a screw type actuator that is engaged with a correspondingly sized threaded aperture extending through the rack arm.

16. A method for adjusting a segment of a spine, comprising:
receiving a surgical system, the surgical system comprising:
a rack arm extending in a longitudinal direction from a first end to a second end, the rack arm including a spline portion;
a sliding body including a ratcheting mechanism having a first actuator and a pawl selectively engageable with the spline portion of the rack arm, the first actuator comprising a rotatable gear meshed with the spline portion and configured to translate the sliding body along the rack arm in the longitudinal direction;
a first connection tower, the first connection tower extending along a first axis transverse to the longitudinal direction and being coupled to the rack arm;
a second connection tower, the second connection tower extending along a second axis transverse to the longitudinal direction and being coupled to the sliding body;
an adjustment mechanism configured to facilitate movement of the first connection tower along the first axis, the adjustment mechanism comprising a body portion, at least two elongate slots formed through respective sidewalls of the body portion, and an aperture formed in an upper wall of the body portion that is opposed from a lower wall of the body portion,
wherein the second end of the rack arm extends through a first slot of the at least two elongate slots formed through the sidewalls of the body portion, and a pivot structure protruding out from the second end of the rack arm extends through a second slot of the at least two elongate slots formed through the sidewalls of the body portion; and
a second actuator including a threaded screw configured to adjust the first connection tower along the first axis;
implanting a first bone fastener system in a first vertebra;
implanting a second bone fastener system in a second vertebra;
attaching the first connection tower to the first fastener system;
attaching the second connection tower to the second bone fastener system; and
manipulating the first vertebra by adjusting the second actuator thereby moving the first vertebra in a sagittal plane.

17. The method of claim 16, further comprising distracting a disc space between the first vertebra and the second vertebra by moving the sliding body along the rack arm upon rotation of the first actuator.

18. The method of claim 17, further comprising adjusting at least one of the first connection tower and/or the second connection tower to manipulate a lordotic orientation of the first vertebra and the second vertebra.

19. The method of claim 17, further comprising adjusting at least one of the first connection tower and/or the second connection tower to manipulate a kyphotic orientation of the first vertebra and the second vertebra.

20. The method of claim 16, further comprising securing a rod to a first connector of the first bone fastener system and a second connector of the second bone fastener system after the manipulating the first vertebra step.

* * * * *